United States Patent [19]

Leonard

[11] Patent Number: 4,913,793
[45] Date of Patent: Apr. 3, 1990

[54] REFERENCE ELECTRODE AND METHOD OF MAKING SAME

[75] Inventor: John E. Leonard, Irvine, Calif.
[73] Assignee: Broadley-James Corporation, Santa Ana, Calif.
[21] Appl. No.: 816,378
[22] Filed: Jan. 6, 1986

Related U.S. Application Data

[63] Continuation-in-part of Ser. No. 774,546, Sep. 10, 1985.
[51] Int. Cl.⁴ ............... G01N 27/30; G01N 27/46
[52] U.S. Cl. ............... 204/433; 204/301; 204/416; 204/435; 204/153.21
[58] Field of Search ............... 204/180.1, 301, 418, 204/435, 433, 416, 419

[56] References Cited

U.S. PATENT DOCUMENTS

| Re. 24,222 | 9/1956 | Patnode et al. | 204/418 |
| 2,614,976 | 10/1952 | Patnode et al. | 204/418 |
| 2,927,887 | 3/1960 | Proctor, Jr. | 204/435 |
| 3,498,899 | 3/1970 | Kater et al. | 204/420 |
| 3,546,087 | 4/1970 | Friconneau et al. | 204/420 |
| 3,681,025 | 8/1972 | Dalgaard | 436/150 |
| 3,686,091 | 8/1972 | Sawa et al. | 204/435 |
| 3,703,457 | 11/1972 | Niedrach et al. | 204/415 |
| 3,730,868 | 5/1973 | Niderach | 204/415 |
| 3,800,410 | 4/1974 | Niedrach et al. | 29/570.1 |
| 3,856,649 | 12/1974 | Genshaw et al. | 204/418 |
| 3,911,901 | 10/1975 | Niedrach et al. | 204/418 |
| 4,002,547 | 1/1974 | Neti et al. | 204/435 |
| 4,105,509 | 8/1978 | Jungek | 204/435 |
| 4,115,209 | 9/1978 | Freiser | 204/418 |
| 4,214,968 | 7/1980 | Battaglia et al. | 204/418 |
| 4,282,079 | 8/1981 | Chang et al. | 204/420 |
| 4,357,143 | 11/1982 | Scott | 204/1 T |
| 4,507,194 | 3/1985 | Shimomura et al. | 204/435 |
| 4,552,625 | 11/1985 | Van Der Velden | 204/435 |
| 4,597,848 | 7/1986 | Oka et al. | 204/418 |

FOREIGN PATENT DOCUMENTS

| 2605149 | 9/1976 | Fed. Rep. of Germany . |
| 3100302 | 12/1981 | Fed. Rep. of Germany . |
| 3228647 | 2/1984 | Fed. Rep. of Germany . |
| 2158905 | 6/1973 | France . |
| 33-8515 | 9/1958 | Japan | 204/301 |
| 54-039155 | 11/1979 | Japan . |

OTHER PUBLICATIONS

Maneham, "Fluoride Electrode as a Reference in the Determination of Nitrate Low", *Analytical Chemistry*, vol. 42, No. 1, Jan. 1970, pp. 128 & 129.
Sigma Chemical Company, St. Louis, MO, 1987 Catalog–Face page, pp. 767–775.
Biorad Corporation, Richmond, CA–1986 Catalog–Face page, pp. 4–29.
Salt Bridges of Porous Glass and Ion–Exchange Membranes, W. N. Carson; C. E. Michelson; Karl Koyama; Anal. Chem. 27, 472–473 (1955).
Ibid, Chemical Abstracts, vol, 49, No. 11, Jun. 10, 1955 (7293f).
Upgrade Your pH Measurements in High–Purity Water, David M. Gray, Power, Mar. 1985, pp. 95–96.
pH Measurements in High Purity Water, Robert C. Hunt, Ultrapure Water, Sep./Oct. 1985; pp. 44–47, 50.
Performance Tests for the Measurement of pH with Glass Electrodes in Low Ionic Strength Solutions Including Natural Waters, William Davison and Woof, Anal. Chem. 1985, 2567–2570.
Physical Techniques in Biological Research, 2nd Edition, vol. 2, Part A; K. S. Spiegler, M. R. J. Wyllie, pp. 353–363, 1968 Academic Press.
Brochure, Xerotyt Reference System–Ingold GmbH & Co, KG.

*Primary Examiner*—T. Tung
*Attorney, Agent, or Firm*—Knobbe, Martens, Olson & Bear

[57] ABSTRACT

A reference electrode, optionally in combination with a measuring electrode to form a combination electrode, is disclosed in which the salt bridge comprises anionic and cationic ion exchange polymer. This polymer may be a diaphragm forming the liquid junction structure of the reference electrode. Polymer is preferably a mixture of anionic and cationic ion exchange polymer which may be either water insoluble or water soluble and is preferably converted to a form which binds equitransferent ions. When the polymer is substantially insoluble, a water-soluble thickener polymer may be incorporated in the polymer composition. Methods of measuring pH using the electrodes of the invention are also disclosed, particularly in high purity deionized water.

35 Claims, 8 Drawing Sheets

REFERENCE ELECTRODE AND METHOD OF MAKING SAME

CROSS REFERENCE TO RELATED APPLICATION

This application is a continuation-in-part application of Ser. No. 774546, filed Sept. 10, 1985 and titled Reference Electrode.

BACKGROUND OF THE INVENTION

This invention is concerned with reference electrodes and in particular with a novel salt bridge and liquid junction structure for such electrodes which comprises anionic and cationic polymer.

The reference electrode is a necessary part of instrumentation systems used in the measurement of electrochemical potentials in analytical laboratories and industrial process control systems. The stability of the reference electrode potential is often the major factor which determines the precision of the measurement. In order to maintain this stability the internal reference cell must be isolated from direct contact with the various test solutions and kept in a constant ionic environment. This is accomplished by use of a salt bridge which is usually a strong solution of potassium chloride and in which the reference cell is immersed. The salt bridge solution must have a constant concentration and must also function to make electrochemical contact with the test sample and thus complete the electrical circuit between the reference and sensing electrodes. The salt bridge makes contact with the test solution through some form of porous substance or capillary structure through which the salt bridge solution flows or diffuses slowly.

Many different types of structures have been used to make this liquid junction. A porous plug of material, such as ceramic, wood, porous Teflon, quartz fiber, or a micropore structure is used as the liquid junction. The sample electrolytes make contact either by slow flow of salt bridge solution through the porous structure into the sample, a flowing junction electrode, or by mutual diffusion into the porous structure from each side, a sealed static junction electrode.

The flowing junction electrode is the more stable and reproduceable of these two junction types. When properly designed it performs reliably in most test samples and is preferred for high precision laboratory measurements. It must be maintained, however, by refilling the salt bridge body with electrolyte to restore the solution lost by outflow. This is not a serious inconvenience in laboratory applications. However, in continuous monitoring for industrial pH control it can become a substantial cost factor, both because of the elaborate hardware needed and the necessity for well-trained personnel.

The sealed, static junction system is designed to be maintenance free for the useful life of the salt bridge. These electrodes have the advantage of requiring simple hardware and minimal maintenance. The salt bridge in such electrodes cannot be maintained by the replenishment of the salt bridge electrolyte and will eventually fail due to contamination and/or dilution of the salt bridge. Although electrodes of this design are not as precise and reproduceable as those with flowing junctions, they have an acceptably long life in many routine laboratory measurements where critical precision is not needed. However, situations where temperature and pressure fluctuations occur will greatly shorten electrode life. A few industrial pH control applications exist where these electrodes perform well enough for an acceptable period of time. These are applications where sample composition is not chemically destructive and where temperature and pressure remain relatively constant.

An electrochemical reference electrode must ideally have a constant potential in a variety of test solutions in order for the electrode to qualify as a reference. However, in practice, most reference electrodes do not behave in this manner and often deviate from one given test solution to another. This deviation can often be compensated for by adjustment of the metering controls so as to bring the value back to the apparent constant potential. However, this is clearly no substitution for a better reference electrode and sometimes the deviation is so great that it cannot be corrected for by the range available on the control unit.

Also, the response time to obtain a stable reading in a test sample should be rapid, for convenience. Long response times tend to lead to premature, and therefore inaccurate, readings. Conventional sealed electrodes tend to be relatively slow. In continuous monitoring situations the reading should be as consistent as possible to obtain an accurate measurement. Often conventional reference electrodes drift with time and therefore give uncertain and inaccurate measurements. When calibrating the electrode error is easily introduced by using the first calibration measurement to establish calibration in other samples. In fact, because of the hysterysis effect, prominent in sealed electrodes, the first calibration value could be varying and therefore this will render the other values inaccurate.

Some test samples provide particular difficulties for the reference electrode. In particular, it is extremely difficult to obtain an accurate and consistent pH reading in high purity, deionized water. In boiler feed waters using such water, it is essential that the pH of the water be monitored. Otherwise the boilers become corroded and this requires expensive maintenance and eventually even replacement of the boilers. Moreover, the reference electrode used in such an environment must be reasonably easy to operate and maintain by the personnel involved. For the reasons mentioned above, flowing junction electrodes are awkward to use and maintain. If not maintained properly, particularly in high purity water, the sample ions tend to rapidly penetrate the electrode and make its reading unstable and eventually useless. The intrusion of high purity water, for example, creates a high impedance in the liquid junction. Sealed electrodes irrespective of maintenance suffer from this intrusion of the sample. Measurement of pH in such water has proved so difficult that procedures have been developed which involve adding to the water a trace amount of electrolyte in order to obtain even an approximately stable measurement. This is obviously self-defeating in that the addition of ions to deionized water changes the pH of the water and provide a reading which is not completely representative of the water itself.

The use of charged polymers in electrodes is known. Carson in Anal. Chem. 27, 472–3 (1955) discloses the preparation of electrodes with an anionic ion-exchange membrane or a cationic ion-exchange membrane. Patnode in U.S. Reissue No. 24222 also discloses certain cationic ion-exchange membranes. Niedrach discloses a carbon dioxide sensor in U.S. Pat. No. 3,730,868 and an oxygen sensor in U.S. Pat. No. 3,703,457 with anionic ion-exchange resin between the electrodes and an oxygen sensor in U.S. Pat. No. 3,800,410 with an anionic ion-exchange resin or a cationic ion-exchange resin between the electrodes. Niedrach also discloses in French patent no. 2,158,905 an ion specific membrane electrode in which the electrolyte comprises an immobilized anionic ion-exchange resin. Freiser in U.S. Pat. No. 4,115,209 discloses an electrode in which a coating of anionic ion-exchange resin is prepared on a conductive surface. Chang in U.S. Pat. No. 4,282,079 discloses a planar, multilayer electrode with a hydrophobic ion-exchange resin in the electrolyte layer.

Despite these known structures and the wide variety of other known electrodes, the above-described problems still exist. There is therefore a need for an electrochemical reference electrode which provides accurate reference measurement in a variety of test samples, provides long-term stable readings in difficult samples such as high-purity, deionized water and which requires low maintenance. Such an electrode has now been discovered.

SUMMARY OF THE INVENTION

According to this invention, there is provided an electrochemical electrode comprising anionic and cationic ion exchange polymer.

The electrode of this invention is a reference electrode, which in one embodiment may be combined with a measuring electrode to form a combination electrode. The electrode of this invention is preferably a sealed-type electrode.

More particularly, the electrode of this invention is a reference electrode comprising:

a half cell;

means for making electrical connection to said half cell; and means for making electrochemical connection between the half cell and a material to be measured when the electrode is immersed in that material, the means for making electrochemical connection comprising anionic and cationic ion exchange polymer.

The polymer preferably comprises the salt bridge in the electrode. More preferably, the polymer in combination with a salt solution around the half cell provides the electrochemical connection between that cell and the liquid to be measured through a liquid junction structure. This structure can be a conventional porous structure such as a ceramic material. Alternatively, the polymer can form the liquid junction structure itself by being incorporated in a diaphragm which forms the outer junction of the electrode between the test material and the internal salt bridge. In this embodiment the diaphragm can either cover one end of the electrode or form substantially all of the outer body of the electrode which is to be immersed in the test sample.

The polymer can be a mixture of anionic ion exchange polymer and cationic ion-exchange polymer or can be a polymer which has both ionic functions, i.e., an amphoteric or Zwitterion polymer. From the standpoint of readily available materials and cost, the mixture of polymers is preferred.

The polymer may comprise water insoluble polymer carrying the necessary ionic functionality or it may comprise hydrophilic polymer or, when a mixture of polymers is used, a mixture of these types of hydrophobic and hydrophilic polymers.

Preferably, the polymer is converted into an equitransferent state by exchange with suitable equitransferent ions. This may be accomplished before or after assembly of the electrode. Preferably the relative proportions in the mixture of polymers is such that they are present in substantially equivalent amounts with respect to their relative capacities so as to provide substantially equivalent amounts of equitransferent ions. More preferably, the polymer further comprises a hydrophilic water soluble or swellable polymer which acts as a thickener or binder in the system. This polymer can be anionic, cationic or nonionic.

BRIEF DESCRIPTION OF THE DRAWINGS

Some preferred embodiments of this invention are illustrated in and by the accompanying drawings, in which like reference numerals indicate like parts.

DETAILED DESCRIPTION

Figure 1:
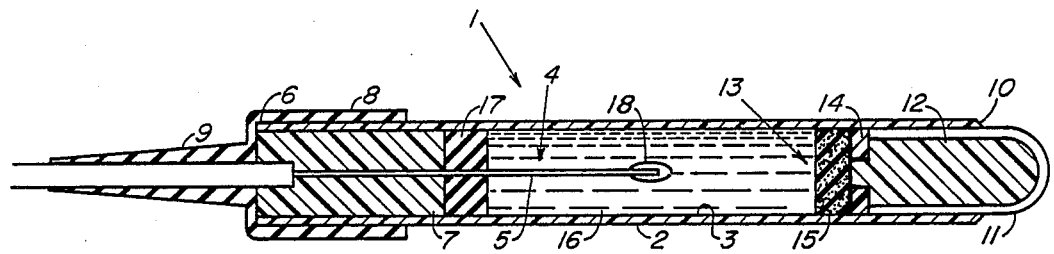
FIG. 1 is a schematic illustration of a reference electrode according to this invention.

Referring first to FIG. 1, there is shown an electrode generally referred to by the numeral 1 and comprising a housing 2 having a generally tubular configuration. Housing 2 is preferably made of a rigid inert plastic material, such as an epoxide, for strength and resistance to damage. Housing 2 forms an internal chamber 3 which contains a half cell 4 formed by a wire 5 which extends through the upper end 6 of housing 2. Wire 5 is sealed into the end 6 by an adhesive material 7 which closes off the end 6 of housing 2. To provide further sealing and strain relief, end 6 is embedded in cap 8 which has an extension 9 projecting therefrom around the wire 5 outside the housing 2 to provide the strain relief to the wire. The lower end 10 of housing 2 is closed by means of porous thimble 11 which forms the liquid junction structure of the electrode 1. Thimble 11 is preferably made of a ceramic material cemented into the end 10 of housing 2. Thimble 11 contains the anionic and cationic polymer material 12. The thimble construction is preferred because it conveniently contains polymer 12. It will be appreciated by those skilled in the art that other types of liquid junction structure could be used. For example, a porous plug or cap across the end 10 of housing 2 or a membrane. Polymer 12 is preferably retained in the lower portion of the housing 2 by retaining means 13, which preferably comprises an annular rubber gasket 14 across the top of thimble 11 snugly fitting within the interior walls of housing 2. Retaining means 13 preferably further comprises a porous synthetic polymer foam plug 15. Plug 15 promotes contact between polymer 12 and a salt solution 16 in chamber 3 above plug 15 and around wire 5 while preventing polymer 12 from dispersing. This is particularly useful when polymer 12 is water insoluble. Preferably, the upper end of chamber 3 is closed by a rubber plug 17 between solution 16 and the adhesive material 7.

Solution 16 may be any conventional electrolyte which can form a reversible equilibrium with the internal half cell. Examples of solution 16 include potassium chloride or ammonium chloride. Other, less common solutions could be used, but it is preferred that solution 16 is a potassium chloride solution, for example 3.8 molar and saturated with silver chloride. This solution may be thickened to form a gel, as is conventional to resist loss of salt bridge from an electrode, for example with about 5% by weight of carboxymethyl cellulose. Wire 5 is preferably a silver wire whose free end in solution 16 has been coated with silver chloride 18.

Typically, the electrode shown in FIG. 1 is approximately 10 cm long, from the top 6 of the housing 2 to the bottom end of the electrode, and about 12 mm across the outside diameter of housing 2.

Figure 2:
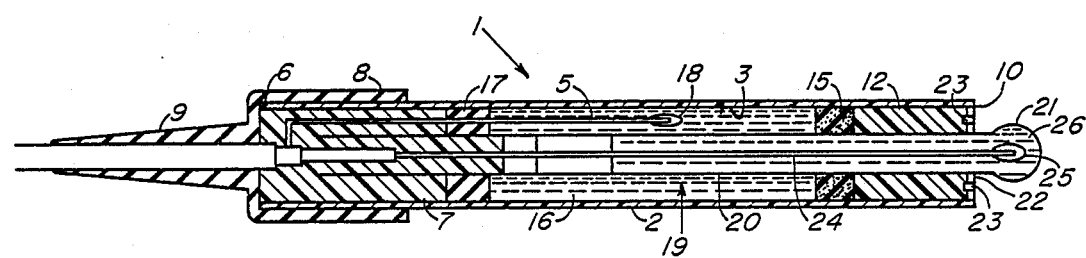
FIG. 2 is a schematic illustration of a combination electrode according to this invention.

Referring to FIG. 2, there is shown a combination electrode according to this invention which includes a measuring half cell 19 which comprises a tube 20 extending down the center of housing 2. The upper end of tube 20 extends through the center of plug 17 and is embedded in adhesive 7 at the upper end 6 of housing 2 so that the upper end of tube 20 is sealed by adhesive 7. Tube 20 extends down through salt solution 16, and is impervious to that solution, through the center of porous plug 15 and polymer 12 to project beyond the lower end of housing 2 and terminate in an exposed measuring bulb 21. Tube 20 is made from a conventional insulating glass and bulb 21 is made from a pH measuring glass. The lower end 10 of housing 2 around tube 20 is closed by an annular gasket 22 which is preferably made of an inert synthetic polymer, such as polytetrafluoroethylene. Gasket 22 has extending therethrough porous plugs 23, preferably made of ceramic, to allow electrochemical contact between polymer 12 and the sample solution. Bulb 21 contains the tip of a wire 24 which extends through the top of the electrode for electrical connection. Wire 24 is preferably made of silver which has been dipped in silver chloride 25 at its tip to form the other half cell with respect to wire 5 in solution 16. Tube 20 and bulb 2 contain a commercial buffered glass-electrode filling solution 26.

Figure 3:
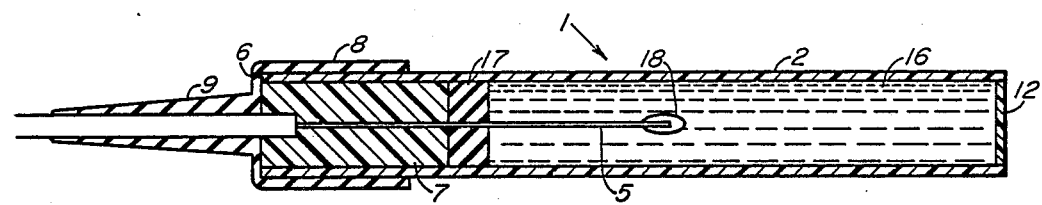
FIG. 3 is a schematic illustration of another embodiment showing an alternative reference electrode according to this invention.

Referring to FIG. 3, there is shown a diaphragm reference electrode according to the invention, which comprises a structure similar to that shown in FIG. 1 except that the polymer 12 forms a membrane across the bottom of housing 2 of the electrode in contact with the internal salt solution 16. Such a construction allows the electrode to be made on a small scale, which is useful in medical and biological applications. Means for mounting diaphragms in such a manner are known in the art. Polymer 12 can be formed into the diaphragm by known techniques. For example, a review of methods of making ion exchange membrane electrodes is given in Physical Techniques in Biological Research, 2nd Edition, Volume 2, Part A, pages 353 to 363, published 1968 by Academic Press, Inc., New York by K. S. Spiegler and M. R. J. Wyllie which is incorporated herein by reference. Thus the polymer can be dispersed in a suitable inert material such as a synthetic polymer, to form the diaphragm.

The anionic and cationic exchange polymer is preferably a mixture of an anionic ion exchange polymer and a cationic ion exchange polymer. Substantially any known ion exchange polymers are appropriate. The polymers may be insoluble polymers, having a hydrophobic backbone, or hydrophilic, substantially water-soluble polymers, or a mixture thereof. The ion exchange functionality may be strong or weak acid for the cationic material or strong or weak base for the anionic material.

The insoluble ion exchange resin polymers are preferably the crosslinked styrene divinylbenzene copolymer type sold under the trademarks Amberlite by Rohm & Haas Company, Philadelphia, Dowex by the Dow Chemical Company of Midland, Mich. and other similar brands by other manufacturers. Suitable polymers in this category include, but are not limited to, Amberlite IR-116; IR-118; IR-120; IR-122; IR-124; IR-130; IR-140; IR-169; IRN-218; IRN-163; and IRP-69 strongly acidic cation exchangers; Amberlite DP-1, IRC-50, IRC-84, CG-50, IRP-64, and IRP-88, weakly acidic cation exchangers; Amberlite IRA-900, IRA-904, IRA-400, IRA-401, IRA-402, IRA-410, IRA-420, IRA-458, and CG-400 strongly basic anion exchangers and Amberlite IRA-93, IRA-94, IRA-45, IRA-47, and IRA-68, weakly basic anion exchangers; Dowex 1X2, 1X4, 1X8 and 2X8 anion exchangers and Dowex 50-WX2, 50-WX4, 50-WX8, 50-WX12 and 50-WX16 cation exchangers. Similar materials from Bio-Rad Corporation of Richmond, Calif. include their AG-1 and AG-2 series, strongly basic anion exchangers, ther AG-50 and 50-W strongly acidic cation exchangers, their Biorex 70 weakly acidic carboxylic cationic exchangers, their AG3-X4A weakly basic ion exchangers, and their AG11-A8 strongly basic ion plus weakly acidic cation Zwitterion exchanger.

Such individual anionic ion exchange polymers and cationic ion exchange polymers can be mixed together in this invention to form the anionic and cationic polymer. It is usually more convenient, however, to use a material that is already available as a commercial mixture as a monobed or mixed bed resin, for example Amberlite MB1-A or MB3-A from Rohm & Haas Company, Biorex RG501-X8 from Dow or the equivalent AG-501-X8 material from Bio-Rad.

Suitable hydrophilic ion exchange polymers are well known and include, for example, cellulose and other polysaccharide derivatives. Commercial materials include the Sephadex and Sepharose materials from Pharmacia Fine Chemicals, Inc.. Sephadex is a derivative of the polysaccharide dextran. Materials of this type include carboxymethyl Sephadex; diethylaminoethyl Sephadex; a fully quaternized strongly basic ion exchanger sold under the brand name QAE Sephadex; sulphopropyl Sephadex; carboxymethyl Sepharose cation exchanger; and diethylaminoethyl Sepharose anion exchanger. Cellulosic materials are also suitable including, as cation exchangers: carboxymethylcellulose; cellulose phosphate and oxycellulose; as anion exchangers: aminoethylcellulose, diethylaminoethyl cellulose, benzyldiethylaminoethyl cellulose, epichlorohydrintriethanolamine cellulose, polyethyleneimine cellulose, diethyl-[2-hydroxypropyl]-aminoethyl cellulose, and triethylaminoethyl cellulose. Because of their price and availability, carboxymethyl cellulose and diethylaminoethyl cellulose are preferred.

When the salt bridge polymer comprises substantially water insoluble ion exchange polymers, it is preferred that the composition also comprises a binder of thickener polymer, which may be anionic, cationic or nonionic. Preferably, this polymer is substantially inert electrochemically so that it does not appreciably affect the potential of the reference half-cell.

It has been found that the presence of such a polymer improves the performance of the electrode over that achieved by the insoluble polymer alone. It is theorized that this thickener polymer contributes a greater barrier to entry into the electrode of ions from the test sample.

This component may be any of the hydrophilic ion-exchange polymers listed above. Preferred thickeners include synthetic acrylic polymers, gelatin and cellulose and polysaccharide derivatives. Preferably the thickener polymer is a cellulose derivative, such as carboxymethyl cellulose, usually in the form of the sodium salt, diethylaminoethyl cellulose or hydroxyethyl cellulose. Carboxymethyl cellulose is most preferred for its relatively high temperature stability which allows the electrode to be used in applications using such temperatures, for example, where sterilization is required. Other preferred thickeners include xanthan gum, agar gum and sodium alginate.

The amount of this component is that sufficient to thicken the anionic and cationic polymer in the electrode, for example from about 1% to about 10% by weight of the anionic and cationic polymer material, preferably from about 2 to about 5%. The commercial insoluble anionic and cationic polymers contain a substantial proportion of water and can therefore be thickened readily.

This thickened ion exchange polymer can be formed in situ in the electrode, or more conveniently, prior to incorporating the polymer in the electrode. Because the polymer may swell appreciably it is preferred to prepare the material before insertion into the electrode. Materials prepared in the electrode can break the electrode housing if the swelling is excessive.

When one or both of the anionic and cationic polymers is hydrophilic and substantially water soluble, as described above, it is not usually necessary to include in the polymer formulation this relatively small amount of thickener polymer since the larger amount of soluble ion-exchange polymer tends to serve that function. It will still, however, be usual to include a thickener polymer in the salt bridge solution to gel that material.

Preferably, the ion exchange polymer is converted into a form having ions which are bound to the polymer relatively strongly. Preferably the polymer is converted into a equitransferent form. Those skilled in the art will be familiar with suitable equitransferent ions. Thus, it may be necessary to exchange a substantial proportion of the ions on the commercial product with ions suitable for use in the electrodes. This conversion may be made in situ when the polymer forms part of the salt bridge in the electrode, or more conveniently, it is done by treating the polymer with the appropriate ions before assembly of the electrode. Preferred as cations are the alkali metal ions, such as potassium and sodium; ammonium and calcium; and as anions halogen, such as chloride; and nitrate. Particularly preferred is potassium and chloride. The conversion may be made by treating a mixed bed resin with the appropriate ions of by taking separate anion and cation exchange polymers and treating them with the respective suitable anion and cation.

Consequently, typical insoluble ion-exchange polymers in their $H+$ and $OH-$ form are converted, for example, to the $K+$ and $Cl-$ form. Therefore these polymers in this invention may be regarded as exhausted ion-exchange resins which would require regeneration for their normal uses, such as in purifying water.

When a mixture of ion exchange polymers is used, their proportions are preferably substantially equivalent, based upon their relative ion-exchange capacities. Some deviation from equivalence is acceptable provided that the resultant electrode provides suitable readings in a variety of test solutions, for example, those that are described below with reference to FIGS. 4 and 5. Preferably, the electrode of the invention should provide a stable reading of plus or minus 20 millivolts from a given calibration value, more preferably, plus or minus 10 millivolts, particularly preferably plus or minus 5 millivolts in such solutions. Preferably the equivalent ratio of anionic polymer to cationic polymer, based on their relative binding capacities, is from 3:1 to 1:3, more preferably from 2:1 to 1:2, most preferably about 1:1, respectively.

The particle size of the insoluble ion-exchange polymers has been found to have some, although not a major, effect on the performance of the electrodes of this invention. Any normal commercial particle sizes are appropriate in this invention, but the smaller sizes are preferred. Less than about 100 mesh is preferred, more preferably about 200–400 mesh. Thus the packing of these insoluble particles in the electrodes of this invention can have an effect on performance, particularly on the response time of the electrode. It is therefore preferred that such materials are packed tightly in the electrode.

Some specific, preferred examples of the anionic and cationic polymer in the electrodes of this invention include:

(1) Styrene/divinylbenzene copolymer type ion-exchange resin—mixture of strong base and strong acid, in $Cl-$ and $K+$ form, respectively;

(2) as (1) with carboxymethylcellulose, diethylaminoethyl cellulose or hydroxyethyl cellulose thickener;

(3) Styrene/divinylbenzene copolymer type ion-exchange resin-strong base in mixture with carboxymethyl cellulose, in $Cl-$ and $K+$ form, respectively;

(4) Styrene/divinylbenzene copolymer type ion-exchange resin -strong acid in mixture with diethylaminoethyl cellulose, in $K+$ and $Cl-$ form, respectively; and (5) Carboxymethyl cellulose and diethylaminoethyl cellulose mixture, in $Cl-$ and $K+$ form, respectively.

The electrodes of this invention can be used separately or in combined construction with pH or other ion-selective electrodes or oxidation-reduction electrodes.

The polymer in the electrodes of this invention is suitable for any half cell chemistry. Thus the half cell may be, for example, silver/silver chloride (which is preferred), mercury/mercurous chloride, mercury/mercurous sulfate or platinum/potassium iodide.

In another embodiment of this invention there is provided a method of measuring the pH of a liquid, which comprises immersing in that liquid an electrode according to this invention. Preferably, this liquid is high purity water.

A further embodiment of this invention provides a method of excluding test solution ions from a reference electrode which comprises immersing an electrode of this invention in the test solution. Preferably, the test solution is high purity water.

It has also surprisingly been found that an electrode of this invention provides stable, ie non-erratic and non-wavering, reproducible readings when immersed in high purity water for extended periods of time, for example at least one month, such as about six months. Such performance from an electrode is very unusual, since conventional electrodes usually provide poor, erratic readings in deionized water from the outset. In process control with respect to flowing deionized water, for example in boiler feed water in the power industry, the state of the art refillable reference electrodes typically provide a pH reading under constant conditions which fluctuates over about a 0.07 to 0.15 pH unit oscillation or band width, or even more, depending on the skill and frequency with which the electrode is maintained. This means that the readout of pH under these conditions is difficult to read accurately and difficult to use as a process control means because the width of the zig zag and erratic line on a pen recorder makes reading the true pH uncertain. The electrode of this invention, however, provides a non-erratic, substantially straight and non fluctuating line under the same conditions. The electrode of this invention provides such a pH reading which typically fluctuates over a width of less than 0.035 pH units under substantially constant pH conditions, preferably less than 0.017 pH units, most preferably less than 0.008 pH units. This degree of stability provides an accuracy which is valuable in industry, particularly in the power industry where such precision can extend the life of expensive equipment, such as the ion exchange beds and the boilers. It will be appreciated by those skilled in the art that the recording equipment can generate a noise signal which can also generate an erratic readout. However, the state of the art equipment is such that such noise signals can be minimized, for example by isolation of the pH analyzer input and output and by external preamplification. Using such good equipment, appropriate for this art, noise can be minimized to an extent that it is not apparent in the readout. The improvements in stability described above are directly attributable to the electrode of this invention because the performance of the electrode can be compared with that of a prior art electrode using the proper equipment.

Upon prolonged exposure to deionized water conventional sealed electrodes fail completely and rapidly due to the intrusion of the water into the electrode under osmotic pressure. A comparable, conventional electrode would be expected to drift 40 mV or more under such circumstances. Despite this pressure, electrodes of this invention can provide acceptable measurements on a continuous long-term basis, for example at least one month and even as long as six months, particularly in flowing deionized water, and even when sealed and no pressure is applied to the electrode to counter that of the deionized water.

One aspect of this invention therefore provides a reference electrode which provides a stable, non-erratic reading in deionized water, as compared with the erratic signal which is customary from conventional reference electrodes. Such electrodes provide a fluctuating reading which is a source of error. In a moving chart-recorder read-out conventional electrodes produce an erratic, zig-zag readout whereas the electrodes of this invention produce a stable readout line which is free of erratic fluctuations to the extent that the band width of the line is substantially the same as that of the pen of the recorder.

Thus the electrode of this invention is characterized by having the ability to maintain an acceptably stable, low liquid junction potential in deionized water on a long term basis.

Thus the anionic and cationic polymer in the electrode of this invention can be regarded as a substantially ion-impermeable membrane. Moreover, it has been found that the electrode of this invention responds extremely quickly to the test material even in its preferred sealed form. Typically, known sealed electrodes take a substantially longer time to come to equilibrium in a new test sample compared with state of the art flowing junction electrodes in a similar sample. It has been found that the sealed electrodes of this invention generally respond like a flowing junction electrode, rather than at the slower rate, as would be expected by a sealed electrode. Error often arises in the use of conventional sealed electrodes because the operator does not wait long enough for the electrode to stabilize. The sealed electrodes of this invention therefore provide a method of improving accuracy by improving the response time to stabilize in a test solution.

According to a preferred embodiment of the invention there is provided a reference electrode comprising anionic and cationic ion exchange polymer, as defined above, which will achieve within 1 mV of its stable potential in a test material in less than five minutes. Preferably that test material is deionized water and the time is preferably less than two minutes, more preferably less than one minute. The invention therefore also provides a method of rapidly measuring pH with such an electrode, preferably in deionized water.

Electrodes of this invention typically reach within 1 mV of their stable values about 10 times as fast as conventional sealed reference electrodes in deionized water, preferably about 100 times as fast.

In the following examples an assessment was made of various polymer compositions in a reference electrode to generate the data listed in Table I, II and III and shown in FIGS. 4 to 9. Examples 3 to 7 and 10 to 31 illustrate some preferred embodiments of the invention. Examples 1, 2, 8 and 9 are comparative examples. Unless otherwise specified, in these examples a reference electrode was constructed using Pyrex tubing approximately 13 centimeters long and having an outside diameter of about 10 millimeters. One end of the tubing is sealed by a vinyl cap through which was passed a silver wire which had previously been dipped in silver chloride. The other end of the tubing was closed by a membrane of dialysis cellophane obtained from the VWR Scientific, Inc. of San Francisco, Calif. No. 727327, and held in place over the end of the tube with a vinyl sleeve. Behind the membrane was packed about 12 mm along the tube of the test polymer, using about 0.8 grams of material. The polymer was held in place by a porous vinyl foam retainer plug between the polymer and 3.8 molar silver chloride thickened with carboxymethyl cellulose to form a gel in contact with the plug and around the silver wire. Dialysis cellophane was chosen as the membrane to provide a simple test body and allow rapid bench measurements to determine the performance of the various polymer compositions. These test electrodes were immersed in various test solutions and their potentials measured against a 9023 refillable reference electrode with a flowing junction salt bridge, available from Broadley-James Corporation, Santa Ana, Calif. recording the output until equilibrium was reached. All measurements were made on static samples without stirring. The test solutions were 1.9 molar potassium chloride; pH 7.0 buffer; pH 4.01 buffer; pH 10.00 buffer; deionized water, having a pH of about 5.8; 10% sodium sulfate, having a pH of about 7.0; 0.1N hydrochloric acid, having a pH of about 1.1; and saturated calcium hydroxide solution having a pH of about 12.4. Each test electrode was stored in 1.9M potassium chloride between test runs and returned to 1.9M potassium chloride between each test so as to normalize and check the electrode. Before immersion in a test sample, the electrode was taken from the potassium chloride and rinsed with deionized water.

EXAMPLE 1

Strong base anionic ion exchange resin AG-1-X8 from Bio-Rad, 200–400 mesh, was obtained in its chloride form and washed acid free.

About 0.8 gram of this resin alone was tested in the test electrode described above. Its stable voltage was typically more than plus 30 millivolts, as shown by line 1 in FIG. 4, and the stable voltage varied widely from one test solution to another. Thus, it was demonstrated that the anionic resin alone was unsuitable for a reference electrode.

EXAMPLE 2

50 grams of Bio-Rad AG50W-X8 strong acid cationic ion exchange polymer having 200–400 mesh was converted into its potassium form by treating the resin with 100 ml of 3.8M potassium chloride. This amount of KCl is approximately 2.7 times that amount required to be equivalent to the 50 g of resin, based upon the capacity of the resin. The resultant material was washed with deionized water until the wash water pH approached that of deionized water, indicating that the excess KCl had been removed.

About 0.8 grams of this resin were placed in the test electrode. The performance of this electrode is shown by line 2 in FIG. 4. It can be seen that the results produced are substantially a mirror image of the anionic resin in line 1, demonstrating that this cationic resin alone is equally unsuitable in the reference electrode.

EXAMPLE 3

44.4 g of Bio-Rad AG50W-X8 was treated with 150 g of 3.8M KCl solution to convert the resin into its potassium form. The product was washed with deionized water until the conductivity of the wash liquor indicated that a negligible amount of the excess KCl was left in the resin. The resin was aspirated on a Buchner funnel and then mixed with 55.6 g of Bio-Rad AG-1-X8 in its chloride form, washed free of acid.

The proportion of these two components was determined from the manufacturer's specifications for the relative capacities of the two resins so as to provide a substantially equivalent mixture of the two resins. Bio-Rad AG50W-X8 has a capacity of 5.1 meq/dry gm, 1.7 meq/ml of resin bed and a water content of 50 to 56%. AG-1-X8 has a capacity of 3.2 meq/dry gm, 1.4 meq/ml of resin bed and a water content of 39 to 45%. Mean water content values were used from the published ranges.

Figure 4:
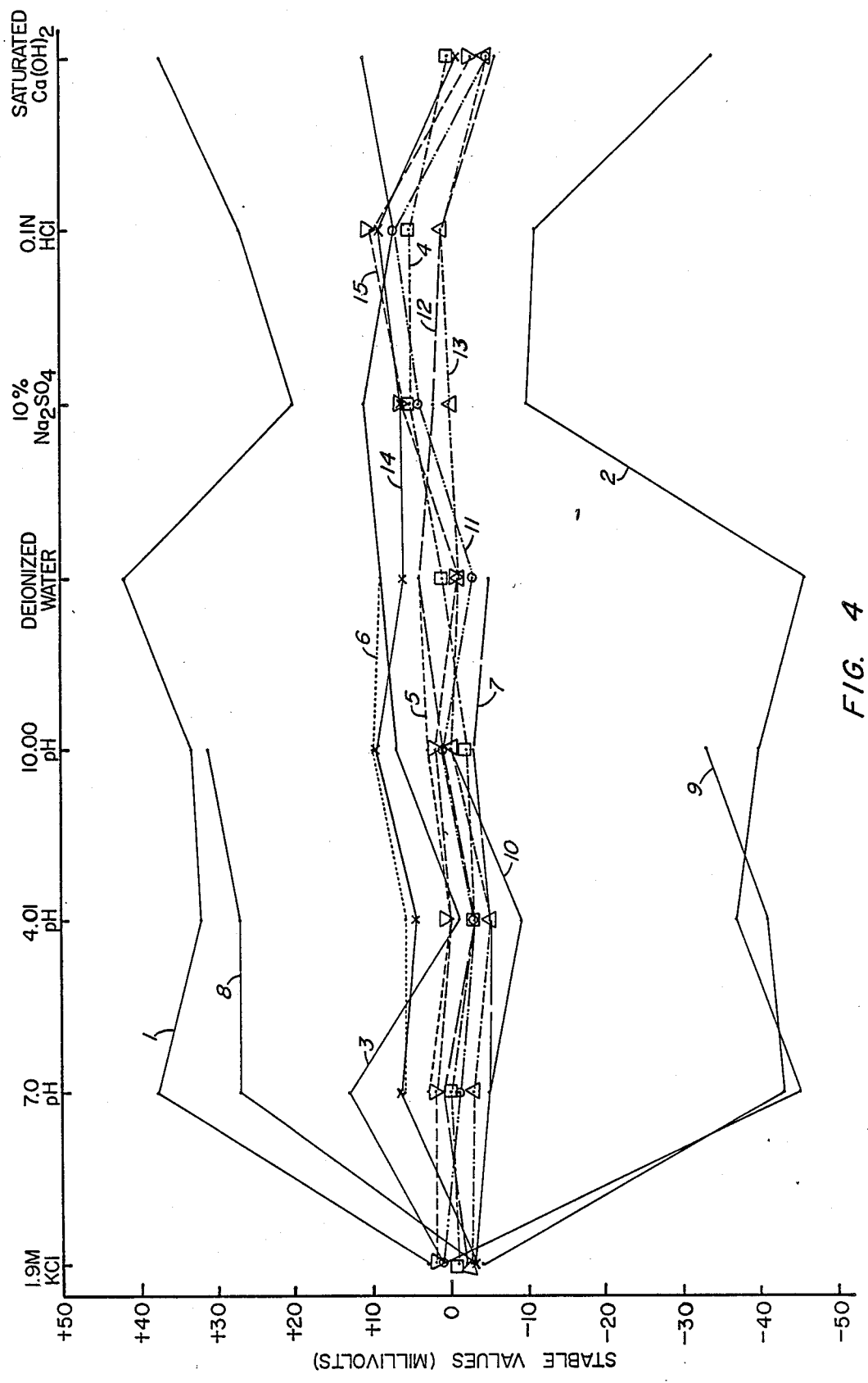
FIG. 4 is a plot of stable reference electrode voltage in various test samples and for various constructions of electrodes, including those according to the present invention.
Figure 5:
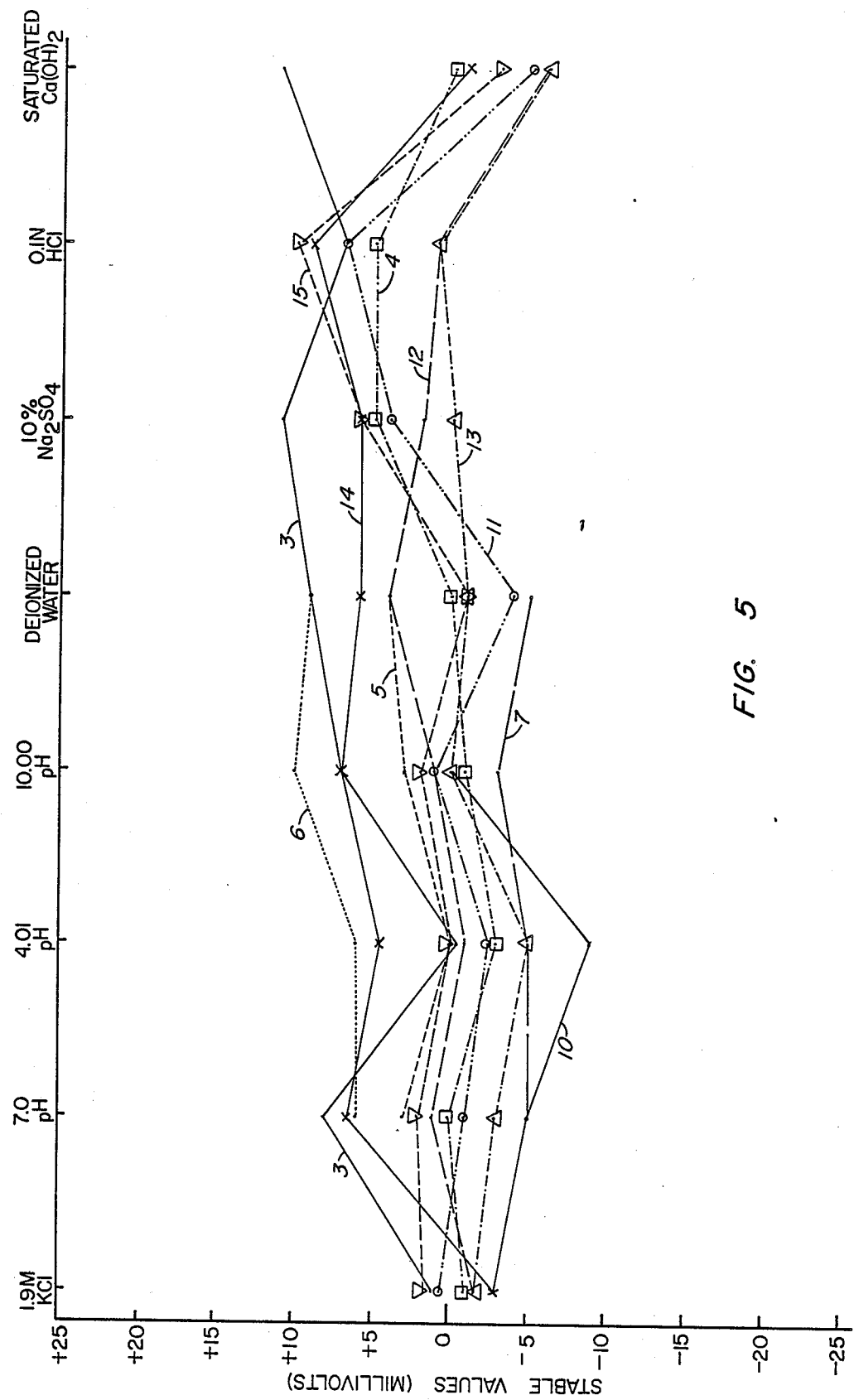
FIG. 5 is a plot of a portion of FIG. 4, but on an expanded scale.

Performance of this polymer is shown by line 3 in FIGS. 4 and 5. It can be seen in FIG. 4 that the electrode provides dramatically better results than the anionic or cationic ion exchange resins alone in Examples 1 and 2. The stable voltages of this electrode ranged from +13 millivolts to −1 millivolts, as can be seen in Table 1.

EXAMPLE 4

25 grams of the polymer mixture of Example 3 was mixed with 2% by weight of that polymer of carboxymethyl cellulose obtained from Hercules, Inc.

It can be seen from line 4 in FIGS. 4 and 5 that the performance of the electrode improved over that of Example 3 to provide a series of usually low, stable values. These values range from no more than plus 5 millivolts to minus 3 millivolts.

EXAMPLE 5

25 grams of the polymer mixture of Example 3 were mixed with 2% by weight of that polymer of hydroxyethyl cellulose to produce the results indicated by line 5 in FIGS. 4 and 5. The variation in voltage found for the solutions tested was from zero to +4 millivolts, indicating a very useful reference electrode.

EXAMPLE 6

50 grams of Amberlite MB-1A mixed bed ion exchange resin, obtained from Sigma Chemical Co., St. Louis, Mo., were converted to the potassium and chloride form by treatment with 75 grams of 3.8 molar potassium chloride. The resultant mixture was washed five times with 100 ml of deionized water and aspirated on a Buchner funnel.

This resin has a coarser particle size than previous examples. Its wet mesh size is from 16 to 50. It can be seen that the performance of this material, as illustrated by line 6 in FIGS. 4 and 5 is not quite as good as the finer mixture in Example 3, but nevertheless provided a very useful reference electrode.

EXAMPLE 7

25 grams of monobed resin in the potassium and chloride form from Example 6 were mixed with 2% by weight of carboxymethyl cellulose from Hercules, Inc. and incorporated in the test electrode.

The carboxymethyl cellulose contributed to improve the performance of the electrode over that achieved in Example 6, as shown by line 7 in FIGS. 4 and 5.

EXAMPLE 8

10 grams of Bio-Rad AG-1-X8 anion exchange resin in its chloride form and washed free of acid, as in Example 1, were mixed with 2% by weight of carboxymethyl cellulose and incorporated in the test electrode provided line 8 in FIG. 4 in the solutions tested.

It can be seen that the performance of this material is similar to the anionic resin alone from Example 1 and therefore demonstrates that the presence of 2% carboxymethyl cellulose does not significantly improve the anionic resin alone.

EXAMPLE 9

In a similar fashion to Example 8, 10 grams of the cationic resin from Example 2 were mixed with 2% by weight of carboxymethyl cellulose to generate line 9 in FIG. 4.

Again, the performance of this material is similar to the cationic resin alone in Example 2.

EXAMPLE 10

100 grams of Bio-Rad AG-501-X8 mixed bed resin were treated with 150 g of 3.8M KCl solution to convert the resin into its K+, Cl− form. The mixture was washed serially with 50 ml aliquots of deionized water until conductivity measurements of the wash water determined that the excess KCl had been removed from the resin. The resin was aspirated on the Buchner funnel.

10 g of this resin in potassium and chloride form were mixed with 2% by weight of carboxymethyl cellulose.

Bio-Rad AG-501-X8 is a mixed bed resin having a dry mesh from 20 to 50 and is therefore relatively coarse.

On the solutions tested, a test electrode including this material produced line 10 in FIGS. 4 and 5, in which the value ranged from 0 to −9 millivolts. Thus a useful electrode was produced.

EXAMPLE 11

20 g (two parts by weight) of carboxymethyl cellulose and 10 g in chloride form (one part by weight) of Bio-Rad anionic exchange resin AG-1-X8 were mixed together to produce a substantially equivalent mixture. These relative proportions were determined by the manufacturers' relative capacity ratios. To this mixture was added 50 grams of 3.8 molar potassium chloride solution to produce a polymer comprising water-soluble cationic polymer in a mixture with water insoluble anionic polymer, in their potassium and chloride forms, respectively. The product was a stiff gel.

The performance of this material is shown by line 11 in FIGS. 4 and 5. The values ranged from −3 to +7 millivolts. Thus an excellent electrode was produced.

EXAMPLE 12

9.5 g (1.9 parts) of diethylaminoethyl cellulose were mixed with 5 g (one part) of Bio-Rad AG-50W-X8 cationic ion exchange resin, to produce a substantially equivalent mixture, as determined by the manufacturers' relative capacities. The product was treated with 50 g of 3.8M KCl and the mixture was filtered and washed with 4×50 ml. of deionized water to obtain a resilient mass and remove the excess KCl. This formed a mixture of water soluble anionic polymer and water insoluble cationic polymer in their chloride and potassium forms.

The performance of this material in the test electrode is illustrated by line 12 in FIGS. 4 and 5. The values ranged from −6 to +4 millivolts. Thus an excellent electrode was produced.

EXAMPLE 13

5 g (1.2 parts) of carboxymethyl cellulose were mixed with 6.35 g (one part) of diethylaminoethyl cellulose to produce a substantially equivalent mixture, as determined by the manufacturers relative capacities. To this mixture were added 50 grams of 3.8 molar potassium chloride solution. The product was filtered and washed, as in Example 12, to form a mixture of water soluble anionic polymer and water-soluble cationic polymer in their chloride and potassium forms.

The performance of this material in the test electrode is shown by line 13 in FIGS. 4 and 5. The values ranged from −5 to +1 millivolts. It can be seen that an excellent reference electrode was produced.

EXAMPLE 14

2 grams of carboxymethyl cellulose were mixed with 8 grams of Bio-Rad AG-1-X8 anionic ion exchange resin in its chloride form, washed free of acid, to form a mixture of water soluble cationic polymer and water insoluble anionic polymer in a ratio of 20 to 80.

This material in the test electrode produced values shown on line 14 in FIGS. 4 and 5. It can be seen that these results are similar to those of the corresponding equivalent mixture in Example 12.

EXAMPLE 15

In a similar manner to Example 14, 4 grams of carboxymethyl cellulose were mixed with 6 grams of Bio-Rad Ag-1-X8 anionic ion-exchange polymer, in its chloride form washed free of acid, to produce a 40/60 mixture.

This material in the test electrode produced values shown in line 15 in FIGS. 4 and 5. It can be seen that these values are similar to those of Example 12.

EXAMPLE 16

A flow cell was constructed with three electrodes; the first was a combination electrode having both glass and reference function, no. 9093 sealed electrode available from Broadley James Corporation; the second was a single measuring glass electrode, no. 9001 from the same company; and the third a ceramic thimble reference electrode, similar to that shown in FIG. 1 and containing the polymer of Example 4. It is known from other measurements that the glass electrodes of the 9001 and 9093 electrodes have the same performance.

The initial, static readings were as follows:

| 9001 glass compared with Ex 4 reference | 9001 glass compared with 9093 reference | 9093 reference compared with Ex 4 reference | 9093 glass compared with 9093 reference |
| --- | --- | --- | --- |
| 6.60 | 6.50 | 6.55 | 6.50 |

These are initial stable measurements as a sample of deionized water which had been in the cell overnight.

Then 300 ml/min of the deionized water were passed through the cell. The following stable readings were obtained:

| 5.55 | 5.25 | 5.20 | 4.80 |
| --- | --- | --- | --- |

These data show a shift of junction potential in the conventional sealed electrode of about ½ pH unit, or about 30 mV, which does not occur in the example material.

The pH of the water was checked independently with a freshly calibrated electrode pair and was found to be within ±0.05 pH units of the Example 4 value.

EXAMPLE 17

Twenty-five grams of Dowex 11A8, obtained from Sigma Chemical Co., was weighed into a 100 ml flask to which were added 50 ml of 3.8M KCl solution to convert the resin to the potassium and chloride form. The mixture was mixed well and set aside to equilibrate. This resin is a Zwitterion resin containing both strongly basic anion and weakly acidic cation functionality. The material was filtered on a small Buchner funnel and washed with 3.8M KCl. The resin was resuspended in the filter with 50 ml 3.8M KCl and aspirated as dry as possible by running the filter for about ten minutes. 22.5 grams of moist resin were obtained.

Figure 6:
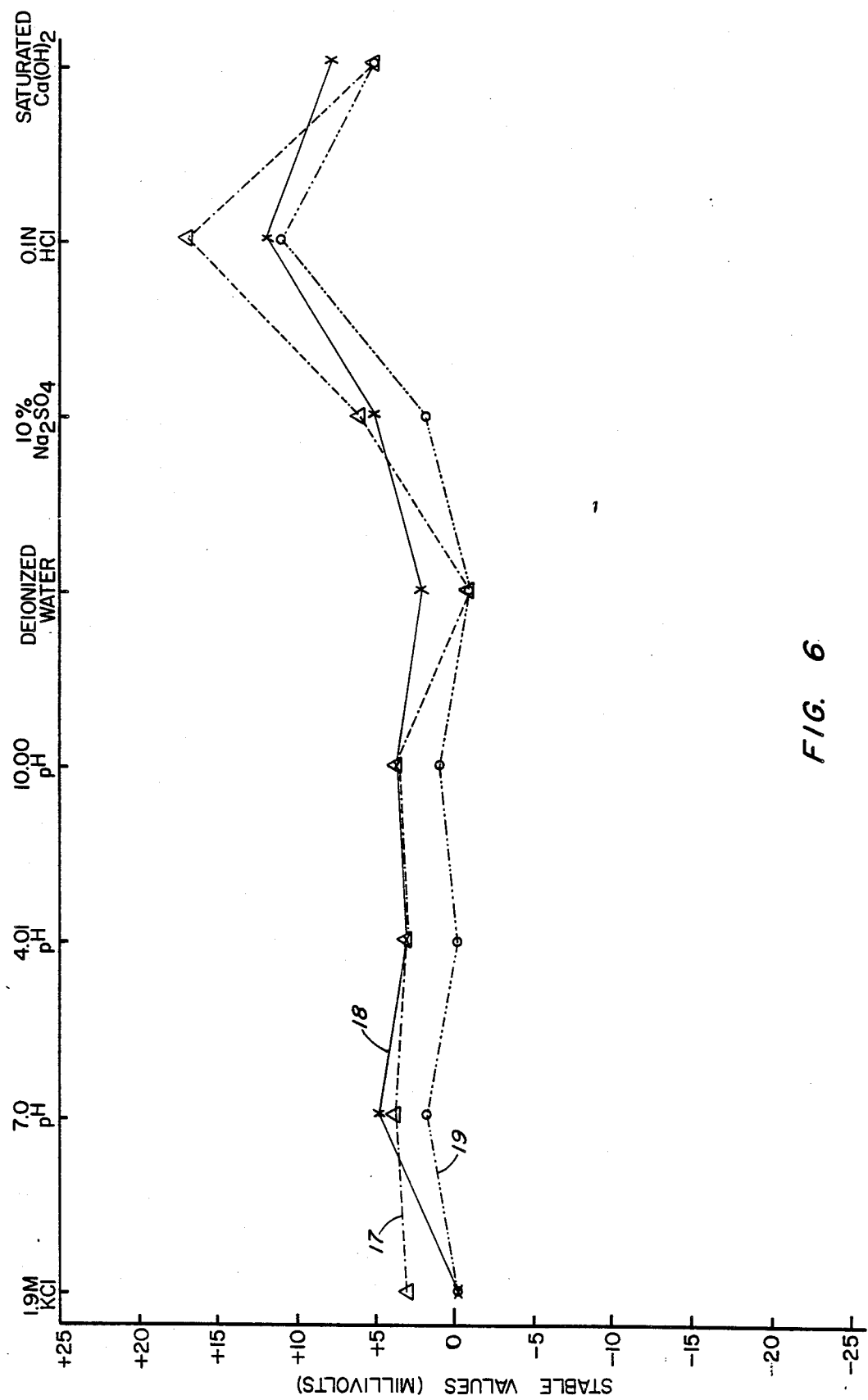
FIG. 6 is a plot of stable voltages of electrodes according to this invention containing containing Zwitterion ion exchange polymer.

This material in the test electrode produced values shown by line 17 in FIG. 6. It can be seen that these values represent a very useful reference electrode.

EXAMPLE 18

In the assembly of the test electrode in the previous example it was found difficult to compress the resin into a compact mass. Tamping the resin tended to cause some resin to flow up the electrode tube. Therefore a further test sample was constructed by mixing the converted resin obtained in the previous example with two percent of resin weight of sodium carboxymethylcellulose thickener.

After standing overnight this material was still rather mobile, as described above, and therefore for convenience an alternative thickener system was used. Literature produced by Hercules Inc. states that an aqueous solution containing one percent each of sodium carboxymethylcellulose and the non-ionic thickener hydroxyethylcellulose, Natrasol 250 MR, have a viscosity about ten times greater than that obtained with either thickener alone. Therefore a test material was prepared by mixing one percent of each of these two thickeners with the converted resin from Example 17.

This material in the test electrode produced values shown by line 18 in FIG. 6. It can be seen that a very useful reference electrode was produced.

EXAMPLE 19

When a new electrode of this invention is first manufactured it can often require several days of soaking in either deionized water or potassium chloride before its potential stabilizes. To observe the effect of heat on the time required to reach stable potentials, the tube of a test electrode was packed with resin from Example 18 between open cell vinyl foam plugs in the tube and topped with 3.8M KCl solution. The assembly was placed in 3.8M KCl solution in a test tube. The test tube was then placed in a water bath and heated to 80 to 90 degrees Centigrade for about one hour. The electrode tube was then removed from the test tube and the contents pushed carefully towards the bottom of the tube until the lower vinyl plug came out and the resin projected slightly from the end of the tube. The tube was then capped with a dialysis membrane to form a test electrode, of the type described above.

The results obtained with this test electrode are shown by line 19 in FIG. 6. It can be seen that a very useful reference electrode was produced. However no significant improvement in the time taken to reach stable potentials was observed although it can be seen from FIG. 6 that the performance of the electrode was improved.

EXAMPLE 20

The effect of varying the proportion of anionic and cationic polymers were studied with various mixtures of Bio-Rad AG1-X8 strongly basic anion exchanger and AG50W-X8 strongly acidic cation exchanger mixtures. The proportions were based upon the manufacturer's specified resin capacity and water content.

18.2 grams of AG1-X8 and 2.0 grams of AG50W-X8 were mixed with 25 grams of 3.8M KCl solution to convert the AG50 resin to the potassium form. The product was a mixture having an equivalent ratio of 6 to 1 anionic to cationic resins, which corresponds to a weight percent ratio of 90.9 to 9.9, respectively. After standing for two hours the mixture was filtered and washed ten times with 50 ml aliquots of deionized water and dried as much as possible on the filter. 20.1 grams of product were obtained. This material in the test electrode produced values shown by line 20(a) in FIG. 7.

In a similar manner a mixture of 3.4 grams of the anionic resin were mixed with 16.6 grams of the cationic resin and treated with potassium chloride to form a mixture having an equivalent ratio of 1 to 6 anionic to cationic, which corresponds to a weight percent ratio of 17.2 to 82.8, respectively. 16.7 grams of product were obtained after filtering and washing. This material in the test electrode produced the line 20(b) in FIG. 7.

Similarly, 15.8 grams of the anionic ionic exchange resin were mixed with 4.2 grams of the cationic exchange resin, treated with potassium chloride, filtered, and washed as described above to produce a mixture having an equivalent ratio of 3 to 1 anionic to cationic resins. This corresponds to a weight percent ratio of 78.9 to 21.1 anionic to cationic resin, respectively. Also, 5.9 grams of anionic resin were mixed with 14.1 grams of cationic resin and mixed with potassium chloride and then filtered and washed to produce a mixture having an equivalent ratio of 1 to 3 anionic to cationic resin, which corresponds to a weight percent ratio of 29.4 to 70.6 anionic to cationic resin, respectively. After standing overnight, neither sample appeared to have been wetted properly by the potassium chloride and low overnight temperatures appeared to have caused potassium chloride crystals to be formed in the mixture. A vacuum was applied to each sample in an attempt to improve the wetting of the materials. However some separation and non-uniformity of the mixtures were still observed caused by the difference in specific gravity of the two resins. Therefore a sample of each mixture was mixed with two percent by weight of sodium carboxymethylcellulose in order to improve the stability of the mixtures so that stable measurements could be obtained. The results obtained with the 3 to 1 anionic to cationic mixture are shown by line 20(c) in FIG. 7 and by line 20(d) for the 1 to 3 anionic to cationic mixture.

Figure 7:
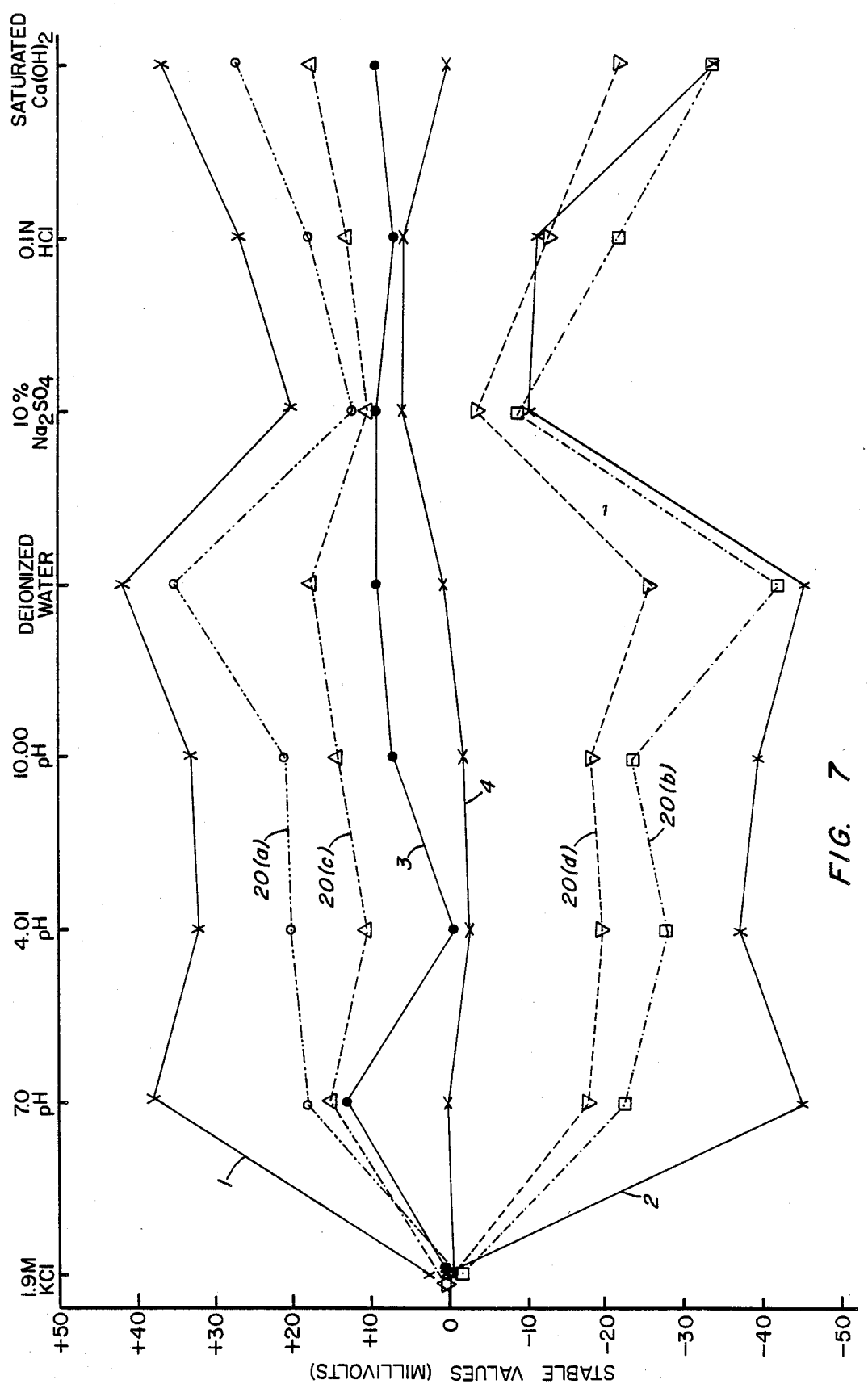
FIG. 7 is a plot of stable voltages of electrodes of this invention containing a mixture of anionic and cationic ion exchange polymers in various relative proportions.

For comparison purposes, there is also shown in FIG. 7 lines numbered 1, 2, 3 and 4 which represent the results obtained from Examples 1 to 4 above, respectively.

The results indicate that the utility in a wide range of test solutions, the equivalent ratio of anionic to cationic polymer in the electrode of this invention is preferably from about 3 to 1 to 1 to 3, more preferably from about 2 to 1 to 1 to 2, most preferably about 1 to 1.

EXAMPLE 21

Ten grams of the 1:1 equivalent resin mixture of Example 3 were mixed with 0.2 grams of xanthan gum solid under the trade name Kelzan by Kelco Chemical Company. The mixture was placed in a test electrode tube and held in place by a vinyl foam plug. The tube was then placed in deionized water to allow the mixture to become moist before completing assembly of the test electrode. On standing the mixture appeared to have become completely wetted and therefore the test electrode was completed and tested to obtain the results shown in FIG. 8 by line 21. It can be seen that a very useful reference electrode was produced.

EXAMPLE 22

Figure 8:
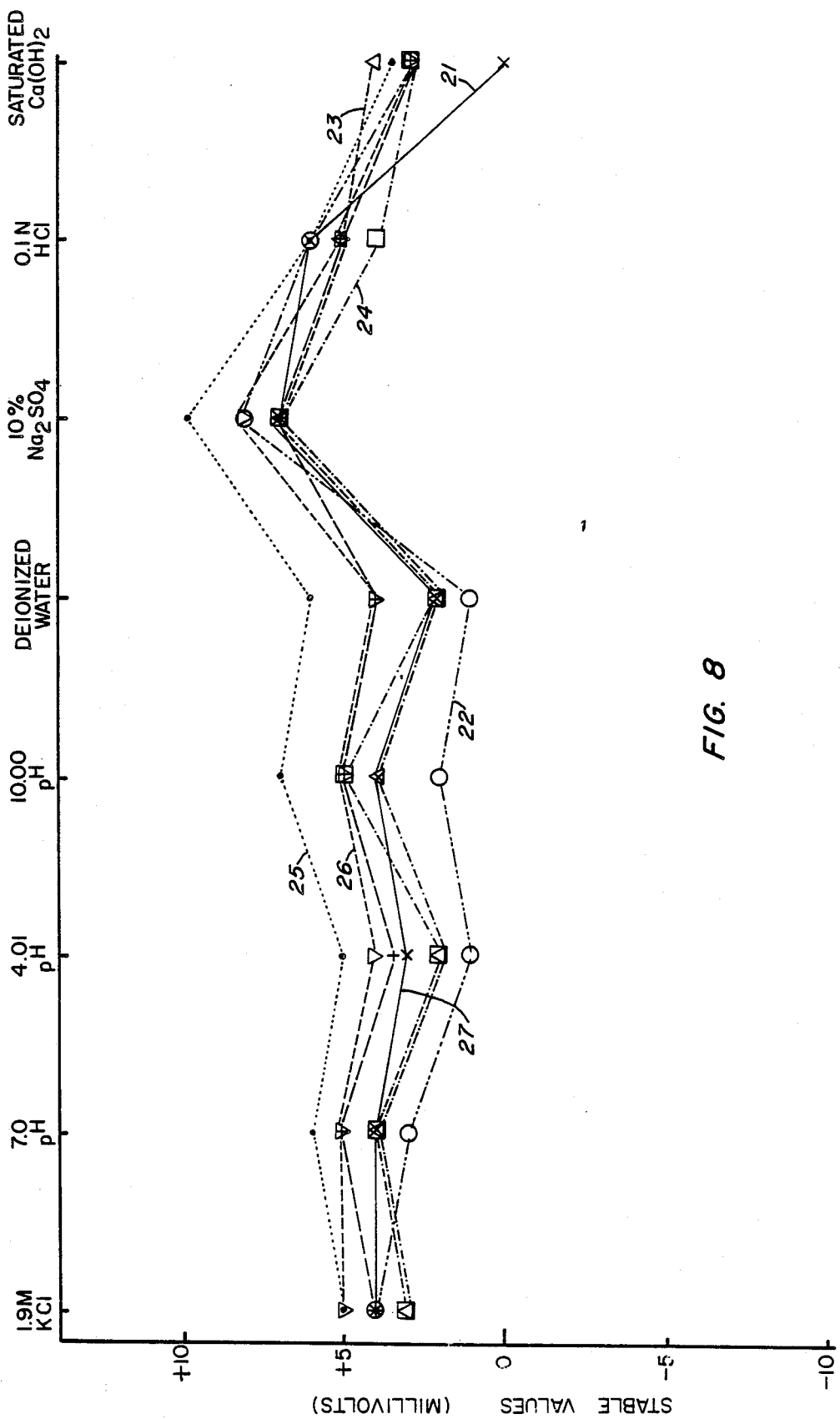
FIG. 8 is a plot of stable voltages of electrodes of this invention containing various thickeners.

In a similar manner to the previous example, a test electrode was prepared containing the mixture of anionic and cationic exchange material from Example 3 and two percent by weight of sodium alginate sold under the trade name Seacor by Stauffer Chemical Company. The results obtained are shown in FIG. 8 by line 22 and are similar to the results in the previous example.

EXAMPLE 23

Following the procedure of Example 21, a test electrode was prepared containing two percent by weight of gelatin thickener on the weight of resin instead of the xanthan gum. The results from the test electrode are shown by line 23 in FIG. 8 and are similar to the previous two examples.

EXAMPLE 24

The procedure of Example 21 was followed except that the xanthan gum was substituted by two percent by weight of the resin of hydroxypropylcellulose sold under the trade name Klucel-MF by Hercules Inc. To make sure that both the resin and the vinyl foam plug in the test electrode were thoroughly wetted, deionized water was also placed above the vinyl plug and the tube placed in deionized water in a beaker. The beaker was then placed in a desiccator to which was applied a vacuum in order to wet the vinyl plug and remove air bubbles from the sample. The deionized water was replaced with 3.8M KCl in the test sample to soak the plug. Then the KCl was replaced by silver chloride gel into which was placed a silver/silver chloride wire to form the test electrode.

The results obtained with this test electrode are shown by the line 24 in FIG. 8. The results obtained were similar to Examples 21–23.

EXAMPLE 25

Following the procedure of the previous example, Reten 210, a synthetic cationic acrylic polymer sold by Hercules Inc, was used as thickener instead of the hydroxypropylcellulose. The results obtained in the test electrode are shown by line 25 in FIG. 8 and are similar to the previous example.

EXAMPLE 26

In similar manner to the previous example Reten 421 was used as the thickener. This is an anionic synthetic acrylic polymer sold by Hercules Inc. The results obtained are shown by line 26 in FIG. 8 and are similar to the previous example.

EXAMPLE 27

Following the procedure of Example 24, Agar obtained from Sigma Chemical Co. was used as the thickener. In the test electrode, the results shown by the line 27 in FIG. 8 were obtained which are similar to the previous example.

It will be noted that the graphs obtained in Examples 21 to 27 are offset from the graph obtained in Example 3 for the non-thickened ion exchange polymer mixture and also from the results obtained in Example 4 for the sodium carboxymethylcellulose thickened mixture. The Example 3 material used in Examples 21 to 27 had been standing for some months since the results were obtained for Example 3 and it is believed that the offset is probably caused by some separation of the two resins during this period.

EXAMPLE 28

About ten grams of each of Bio-Rad AG1 anionic exchanger and AG50 cationic exchanger described above in their potassium and chloride forms were weighed into separate beakers and placed in an oven at 110° Centigrade to dry the resins. The dried resins were weighed and it was determined that the AG1 resin lost about 34.6% of water. The AG50 resin lost about 48.5% water. Using the manufacturer's dry capacity values an equivalent mixture of the two dry resins was prepared by grinding appropriate amounts of the two resins together.

An open ended epoxy tube was taken and a rubber plug cut from a serum cap was placed in one end of the tube. Above that plug was placed a vinyl foam spacer. A vacuum was applied to one end of the tube and through a small hole in the rubber plug. Ground mixed resin was placed on top of the vinyl foam spacer. Then catalyzed epoxy resin was applied to the ion exchange resin mixture and the vacuum maintained until the epoxy resin thoroughly wetted the ion exchange material and all air bubbles were removed from it. The vacuum was then removed and the epoxy resin allowed to cure. A disc approximately 3.5 millimeters thick was then cut from the resin and glued with epoxy resin into the open end of an appropriately sized epoxy tube so as to form an ion exchange membrane across, and sealing, the bottom of the tube. The tube was then filled with silver chloride solution gelled with sodium carboxymethylcellulose and a silver/silver chloride wire placed in the gel. This produced an electrode according to the invention using the anionic and cationic exchange mixture as a membrane.

EXAMPLE 29

Five reference electrodes were constructed using the material of Example 4. The electrodes were sealed electrodes having a ceramic thimble at their tip containing the ion exchange material, as shown in FIG. 1.

A similar, but conventional sealed reference electrode was also constructed containing gelled 3.8M potassium chloride saturated with silver chloride and a silver/silver chloride wire.

The long-term performance of the electrodes was assessed in static, 1.9M potassium chloride and static, deionized water for the electrodes of this invention and in static, deionized water for the conventional electrode.

Figure 9:
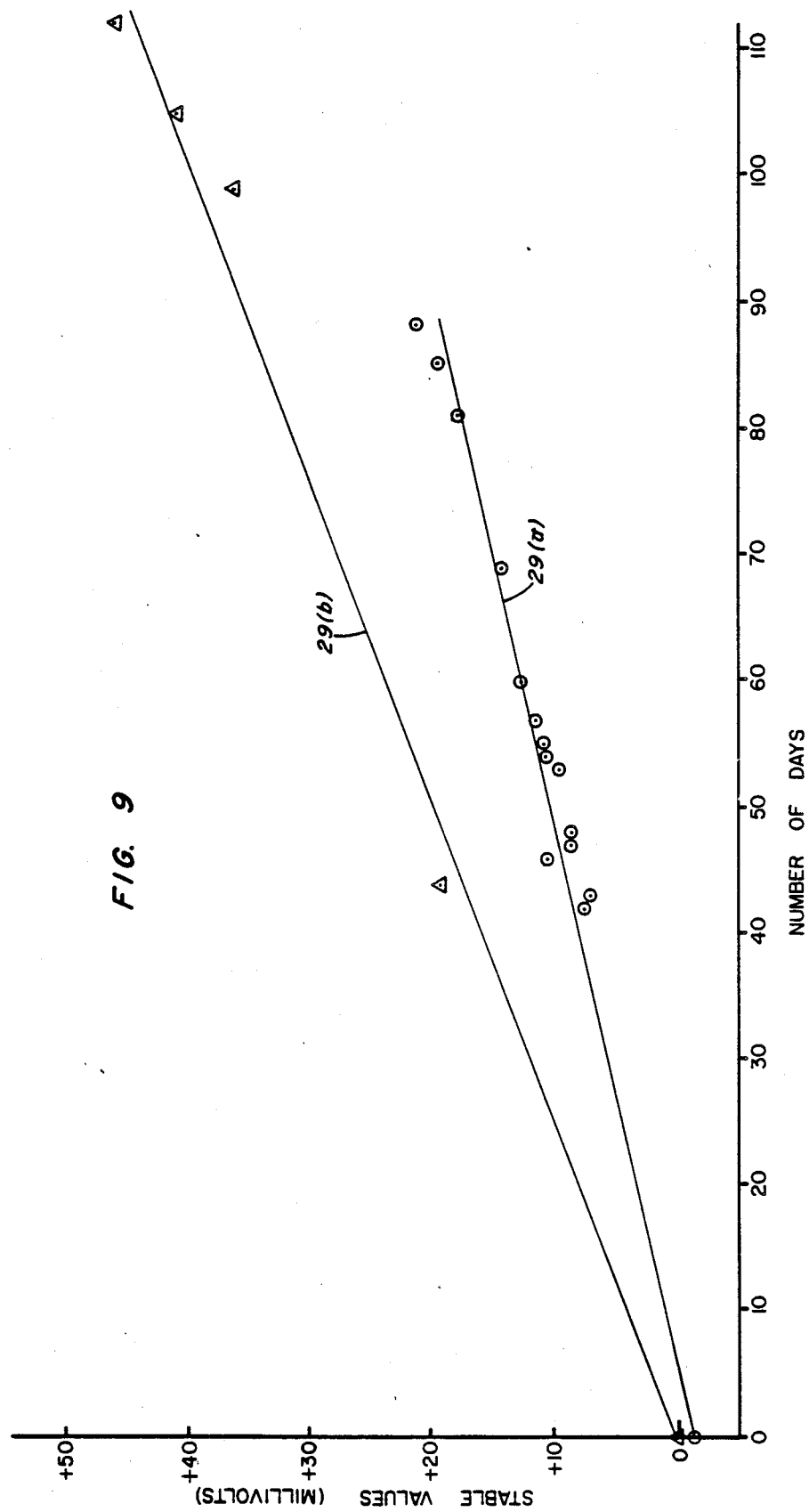
FIG. 9 is a plot of stable voltages over time of a conventional reference electrode and reference electrodes of this invention.

The results are tabulated in Table II and the results in deionized water shown in FIG. 9 by line 29(a) for the mean values of the invention electrodes and line 29(b) for the conventional electrode.

It can be seen that the conventional electrode rather rapidly deteriorates to provide large millivolt values whereas, in comparison, the electrodes of this invention drift substantially more slowly to lower offset potential values.

EXAMPLE 30

The time taken for the electrodes of the previous examples to reach within one millivolt of their final, stable potentials are tabulated in Table III.

These data were also obtained for three conventional sealed reference electrodes, model number 9093 from Broadley-James Corporation.

It can be seen that the electrodes of this invention typically respond as fast, and usually significantly faster than the conventional electrodes. Indeed, in many cases, the response times of the electrodes of this invention are dramatically shorter than those of the conventional electrodes.

In deionized water, which usually causes long response times in conventional reference electrodes, the electrodes of this invention are consistently much faster to respond and reach a stable potential. The data indicate that the electrodes of this invention are typically about 10 times as fast to respond and in many cases as much as 100 times as fast as the conventional sealed reference electrodes.

EXAMPLE 31

The performance of various reference electrodes in the boiler feed water at a power station was assessed and are shown in FIG. 10.

The water was flowing high purity deionized water and the pH recordings shown in FIG. 10 were obtained under the same conditions of flow rate and chart speed. In the Figure, each division in a direction perpendicular to the read out line represents 0.0357 pH units.

Figure 10A:
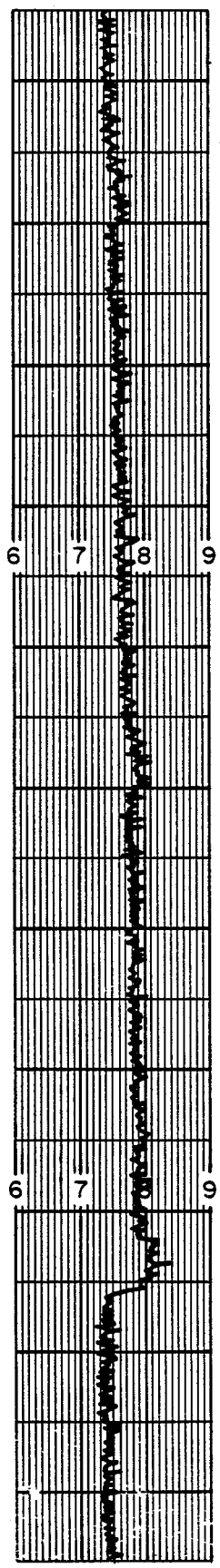
FIG. 10 is a reproduction of chart recorder printouts in the measurement of pH in high purity boiler feed water using a conventional reference electrode and an electrode of this invention.

FIG. 10A illustrates the results normally obtained with a state of the art refillable reservoir, ceramic reference electrode. The large excursion represents the injection of ammonia into the water to correct the pH of the water in response to the pH value determined by the pH meter. It can be seen that the graph is erratic and typically fluctuates over about 4 divisions, or about 0.14 pH units. This fluctuation makes it uncertain what the true pH of the water is and therefore renders inaccurate the pH adjustment.

Figure 10B:
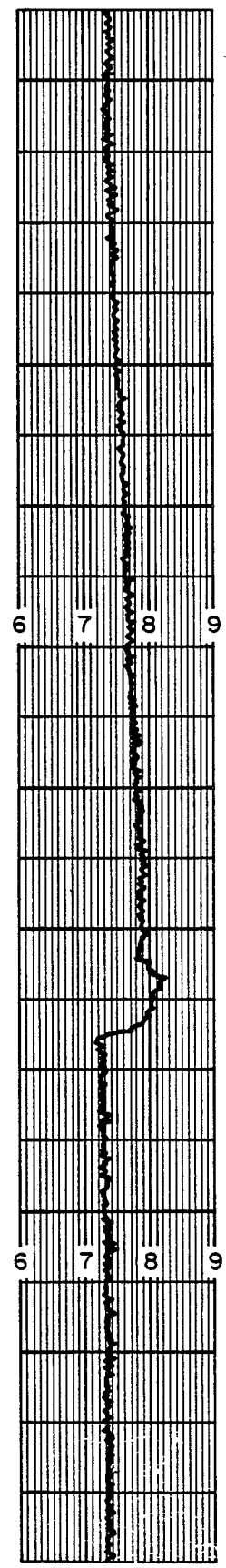

FIG. 10B illustrates the results obtained with the same equipment as in FIG. 10A, but after careful maintenance and selection of the electrode. It can be seen that the graph is still erratic but less so than in FIG. 10A. The width of the average fluctuations in FIG. 10B is about 2 divisions, or about 0.07 pH units. This still represents a source of very significant error.

Figure 10C:
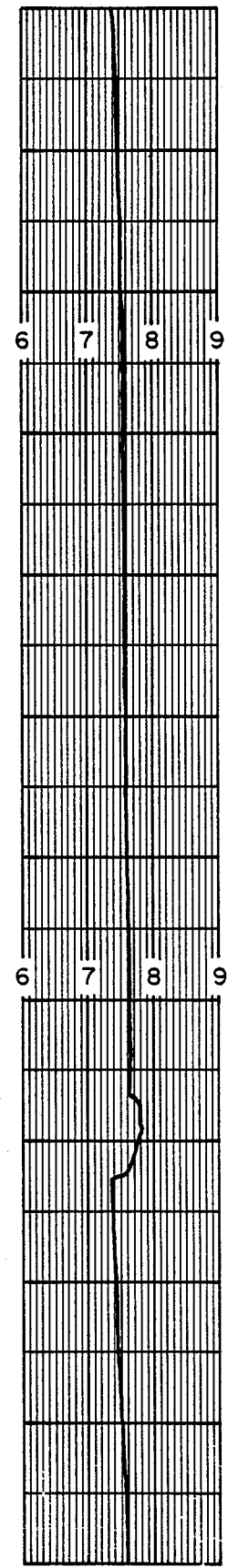

FIG. 10C illustrates the results obtained using an electrode of this invention. The electrode is a sealed reference electrode of the type shown in FIG. 1 and containing ion exchange polymer of Example 4. It can be seen that the graph is dramatically different from those of FIGS. 10A and 10B. The read-out line is free of visible erratic oscillations and allows a substantially improved degree of accuracy and control over the pH. The excursion caused by the addition of ammonia is visibly better defined. This performance allows the pH correction to be achieved more accurately and without significant over adjustment.

TABLE I

| Ex. No. | 1.9 M KCl | 7.0 pH | 4.01 pH | 10.00 pH | DI* $H_2O$ | 10% $Na_2SO_4$ | 0.1 N HCl | Saturated $Ca(OH)_2$ |
|---|---|---|---|---|---|---|---|---|
| 1 | +3 | +38 | +32 | +33 | +42 | +20 | +27 | +37 |
| 2 | +1 | −45 | −37 | −40 | −46 | −10 | −11 | −34 |
| 3 | +1 | +13 | −1 | +7 | +9 | +11 | +7 | +11 |
| 4 | −1 | 0 | −3 | −2 | +0.5 | +5 | +5 | 0 |
| 5 |  | +3 | 0 | +3 | +4 | — | — | — |
| 6 |  | +6 | +6 | +10 | +9 | — | — | — |
| 7 |  | −5 | −5 | −3 | −5 | — | — | — |
| 8 | −1.5 | +27 | +27 | +31 | — | — | — | — |
| 9 | −3.5 | −43 | −41 | −33 | — | — | — | — |
| 10 | −3 | −5 | −9 | 0 | — | — | — | — |
| 11 | +1 | −1 | −3 | +1 | −3 | +4 | +7 | −5 |
| 12 | −1.5 | +1 | −1 | +1 | +4 | +2 | +1 | −6 |
| 13 | −2.5 | −3 | −5 | 0 | −1 | 0 | +1 | −5 |
| 14 | −3 | +6.5 | +4.5 | +7 | +6 | +6 | +9 | −1 |
| 15 | +1.5 | +2 | 0 | +2 | −1 | +6 | +10 | −3 |
| 17 | +3 | +4 | +3 | +4 | −1 | +6 | +17 | +5 |
| 18 | 0 | +5 | +3 | +4 | +2 | +5 | +12 | +8 |
| 19 | 0 | +2 | 0 | +1 | −1 | +2 | +11 | +5 |
| 20(a) | −0.75 | +18 | +20 | +21 | +35 | +12 | +18 | +27 |
| 20(b) | −1.5 | −23 | −28 | −24 | −43 | −9 | −22 | −34 |
| 20(c) | 0 | +15 | +10.5 | +14 | +18.5 | +10.5 | +12.5 | +18 |
| 20(d) | 0 | −18 | −20 | −17.5 | −26 | −4 | −12.5 | −21.5 |
| 21 | +4 | +4 | +3 | +4 | +2 | +7 | +6 | 0 |
| 22 | +4 | +3 | +1 | +2 | +1 | +8 | +6 | +3 |
| 23 | +3 | +4 | +2 | +4 | +2 | +7 | +5 | +4 |
| 24 | +3 | +4 | +2 | +5 | +2 | +7 | +4 | +3 |
| 25 | +5 | +6 | +5 | +7 | +6 | +10 | +6 | +3.5 |
| 26 | +5 | +5 | +4 | +5 | +4 | +8 | +5 | +3 |
| 27 | +4 | +5 | +3.5 | +5 | +4 | +7 | +5 | +3 |

*Deionized water

TABLE II

| Number of Days | Electrode Numbers | | | | | | | | | | Comparative Electrode |
|---|---|---|---|---|---|---|---|---|---|---|---|
|  | 1 | | 2 | | 3 | | 4 | | 5 | | |
|  | KCl | $H_2O$ | KCl | $H_2O$ | KCl | $H_2O$ | KCl | $H_2O$ | KCl | $H_2O$ | $H_2O$ |
| 0 |  |  |  |  |  |  |  |  |  |  | 0 |
| 36 | +9 |  |  |  | +8 |  | +6 |  | +10 |  |  |
| 39 | +12 |  | +11 |  | +11 |  | +8 |  | +13 |  |  |
| 40 | +12 |  | +10 |  | +13 |  | +11 |  | +14 |  |  |
| 41 | +8 |  | +5 |  | +8 |  | +6 |  | +11 |  |  |
| 42 | +9 | +8 | +9 | +6 | +9 | +9 | +6 | +6 | +11 | +9 |  |
| 43 | +9 | +7 | +9 | +4 | +9 | +8 | +6 | +5 | +11 | +11 |  |
| 44 | — | — | — | — | — | — | — | — | — | — | +19 |

TABLE II-continued

| | | | | | | | | | | |
|---|---|---|---|---|---|---|---|---|---|---|
| 46 | +12 | +10 | −13 | +9 | +13 | +12 | +9 | +8 | +15 | +14 |
| 47 | +10 | +8 | +11 | +7 | +10 | +9 | +6 | +6 | +12 | +12 |
| 48 | +10 | +8 | +11 | +7 | +10 | +9 | +6 | +6 | +12 | +12 |
| 53 | +11 | +9 | +13 | +10 | +11 | +10 | +7 | +6 | +13 | +12 |
| 54 | +12 | +10 | +14 | +11 | +12 | +11 | +8 | +7 | +13 | +13 |
| 55 | +12 | +10 | +14 | +12 | +12 | +11 | +9 | +9 | +13 | +12 |
| 57 | +12 | +10 | +15 | +13 | +11 | +10 | +9 | +9 | +14 | +14 |
| 60 | +13 | +12 | +16 | +14 | +13 | +13 | +10 | +9 | +15 | +14 |
| 68 | +15 | +14 | +18 | +17 | +14 | +14 | +10 | +9 | +16 | +16 |
| 81 | +19 | +18 | +24 | +21 | +18 | +17 | +12 | +12 | +19 | +19 |
| 85 | +21 | +21 | +25 | +25 | +20 | +19 | +14 | +14 | +20 | +20 |
| 88 | +23 | +22 | +28 | +27 | +21 | +21 | +16 | +16 | +21 | +22 |

| Number of Days | Mean Value of Electrodes 1-5 | | Comparative Electrode |
|---|---|---|---|
| | KCl | H$_2$O | H$_2$O |
| 0 | — | −1.2 | 0 |
| 36 | +8.6 | — | |
| 39 | +11 | — | |
| 40 | +12 | — | |
| 41 | +7.6 | — | |
| 42 | +8.8 | +7.6 | |
| 43 | +8.8 | +7 | |
| 44 | — | — | +19 |
| 46 | +12.4 | +10.6 | |
| 47 | +9.8 | +8.4 | |
| 48 | +9.8 | +8.4 | |
| 53 | +11 | +9.4 | |
| 54 | +11.8 | +10.4 | |
| 55 | +12 | +10.8 | |
| 57 | +12.2 | +11.2 | |
| 60 | +13.4 | +12.4 | |
| 68 | +14.6 | +14 | |
| 81 | +18.4 | +17.4 | |
| 85 | +20.0 | +19.8 | |
| 88 | +21.8 | +21.6 | |
| 99 | — | — | +36 |
| 105 | | | +41 |
| 112 | | | +46 |

TABLE III
RESPONSE TIMES

| Example Number | 7.0 | 4.01 | 10.00 | Deionized Water | Na$_2$So$_4$ | 0.1 N HCl | Ca(OH)$_2$ |
|---|---|---|---|---|---|---|---|
| 3 | 3 min | 60 min | 21 min | 26 min | 11 min | 2 min | 30 min |
| 4 | 30 sec | 30 sec | 30 sec | 30 sec | 30 sec | 2 min | 1 min |
| 5 | 45 min | 30 sec | 15 min | 4 min | 6 min | 2 min | 6 min |
| 6 | 4 min | 5 min | 11 min | 6 min | 18 min | 8 min | 8 min |
| 7 | 9 min | 7 min | 5 min | 15 min | 2 min | 9 min | 6 min |
| 10 | 8 min | 17 min | 9 min | — | — | — | — |
| 11 | 2 min | 13 min | 11 min | 19 min | 4 min | 30 sec | 9 min |
| 12 | 30 sec | 30 sec | 3 min | 8 min | 3 min | 2 min | 5 min |
| 13 | 5 min | 3 min | 30 sec | 5 min | 30 sec | 2 min | 30 sec |
| 14 | 8 min | 5 min | 15 min | 6 min | 8 min | 11 min | 1 min |
| 15 | 3 min | 4 min | 6 min | 9 min | 30 sec | 2 min | 6 min |
| 17 | 15 min | 22 min | 45 min | 45 min | 2 min | 2 min | 17 min |
| 20(a) | 30 min | 17 min | 45 min | 38 min | 38 min | 34 min | 38 min |
| 20(b) | 30 min | 30 min | 26 min | 49 min | 11 min | 41 min | 19 min |
| 20(c) | 30 min | 11 min | 30 min | 60 min | 20 min | 22 min | 74 min |
| 20(d) | 30 min | 30 min | 22 min | 45 min | 15 min | 45 min | 53 min |
| 21 | 30 sec | 30 sec | 40 min | 30 sec | 40 min | 40 min | 20 min |
| 22 | 30 sec | 9 min | 6 min | 30 sec | 15 min | 30 sec | 4 min |
| 23 | 30 sec | 10 min | 10 min | 30 min | 10 min | 30 sec | 30 sec |
| 24 | 30 sec | 10 min | 10 min | 30 sec | 10 min | 10 min | 30 sec |
| 25 | 2 min | 30 sec | 11 min | 2 min | 9 min | 2 min | 30 sec |
| 26 | 30 sec | 30 sec | 2 min | 6 min | 4 min | 3 min | 30 sec |
| 27 | 30 sec | 10 min | 30 sec | 10 min | 40 min | 10 min | 30 sec |
| ref1 | 5 min | 7 min | 3 min | 60 min | 5 min | 60 min | 7 min |
| ref2 | 5 min | 8 min | 5 min | 45 min | 5 min | 40 min | 8 min |
| ref3 | 8 min | 8 min | 8 min | 50 min | 5 min | 40 min | 8 min |

I claim:

1. A reference electrode comprising:
a half cell;
means for making electrical connection to said half cell; and
means for making electrochemical connection between said half cell and a test material when said electrode is immersed in said material, said means for making electrochemical connection being substantially ion-impermeable and comprising a mixture of anionic ion exchange polymer and cationic ion exchange polymer.

2. An electrode as claimed in claim 1, wherein said means for making electrochemical connection further comprises:
a salt solution around said half cell, said solution and said polymers forming a salt bridge in said electrode;
said electrode further comprising:
a housing containing said salt bridge and having means for providing a liquid junction between said salt bridge and said material.

3. An electrode as claimed in claim 1, wherein said electrode further comprises:
a salt solution around said half cell, said means for making electrochemical connection comprising a diffusion membrane at an extremity of said electrode for making direct contact with said test material.

4. An electrode as claimed in claim 1, in a combination electrode and further comprising:
a measuring electrode having a body forming an internal chamber having an ion permeable measuring portion exposed at one end of said electrode, said chamber containing therein a half cell surrounded by salt solution.

5. A sealed reference electrode comprising: a housing containing:
an electrolyte;
a half cell immersed in said electrolyte; and
a substantially ion-impermeable mixture of anionic ion exchange polymer and cationic ion-exchange polymer, said mixture being in electrochemical contact with said electrolyte and adapted to provide such contact with said water.

6. An electrode as claimed in claim 5, where said electrode provides a substantially stable measurement for at least one month.

7. An electrode as claimed in claim 6, where said electrode provides a measurement for at least six months.

8. A reference electrode, comprising:
an outer body having walls forming an internal chamber, a portion of said walls being permeable to aqueous liquids;
a half cell in said chamber;
a salt bridge in said chamber in electrochemical contact with said half cell; and
means substantially impervious to ions and comprising a mixture of an anionic polymer and a cationic polymer for completing said contact through said portion of said walls with a sample outside said chamber for electrochemical measurements thereof.

9. An electrode as claimed in claim 1, 5 or 8, wherein said mixture is either a water-soluble anionic ion-exchange polymer and a water-insoluble cationic ion-exchange polymer, or a water-insoluble anionic ion-exchange polymer and water-soluble cationic ion-exchange polymer.

10. An electrode as claimed in claim 1, 5 or 8, wherein said mixture comprises a strongly basic synthetic ion-exchange resin and a strongly acidic ion-exchange resin.

11. An electrode as claimed in claim 10, wherein said polymers each comprises cross-linked styrene/divinylbenzene copolymers.

12. An electrode as claimed in claim 1, 5 or 8, wherein the anion of said anionic polymer comprises an ion selected from the group consisting of halogen, nitrate and sulfate, and the cation of said cationic polymer comprises an ion selected from the group consisting of sodium, potassium, ammonium and calcium.

13. The electrode as claimed in claim 1, 5 or 8, wherein the anion of said anionic polymer comprises halogen and the cation of said cationic polymer comprises alkali metal.

14. An electrode as claimed in claim 13, wherein said halogen is chloride and said alkali metal is potassium.

15. An electrode as claimed in claim 1, 5 or 8, wherein said anionic and cationic polymers are present in said mixture in substantially equivalent amounts with respect to their binding capacities for anions and cations, respectively.

16. An electrode as claimed in claim 1, 5 or 8, wherein said anionic and cationic polymers are present in said mixture in an amount of from 3:1 to 1:3, respectively, with respect to their binding capacities for anions and cations, respectively.

17. An electrode as claimed in claim 16, wherein said amount is from 2:1 to 1:2.

18. An electrode as claimed in claim 1, 5 or 8, wherein said mixture comprises an anionic cellulose polymer and a cationic cellulose polymer.

19. An electrode as claimed in claim 18, wherein said anionic cellulose polymer comprises diethyl-aminoethyl cellulose and said cationic cellulose polymer comprises a carboxymethyl cellulose.

20. An electrode as claimed in claim 1, 5 or 8, wherein said mixture comprises a styrene/divinylbenzene copolymer and a cellulose polymer.

21. An electrode as claimed in claim 1, 5 or 8, wherein said mixture comprises an anionic styrene/divinylbenzene copolymer, a cationic styrene/divinylbenzene copolymer and further comprises a hydrophilic thickener polymer.

22. An electrode as claimed in claim 21, wherein said thickener polymer is selected from the group consisting of a carboxymethyl cellulose, xanthan gum, agar gum, gelatin and a synthetic acrylic polymer.

23. An electrode as claimed in claim 21, wherein said thickener polymer comprises a carboxymethyl cellulose.

24. An electrode as claimed in claim 1 or 5, capable of providing a reading of pH in deionized water under substantially constant pH conditions which fluctuates over less than 0.035 pH units.

25. An electrode as claimed in claim 24, wherein said fluctuation is less than 0.017 pH units.

26. An electrode as claimed in claim 1 or 5, capable of providing a stable reading of plus or minus 20 millivolts from a calibration value.

27. An electrode as claimed in claim 26, wherein said reading is within plus or minus 10 millivolts of said value.

28. A reference electrode for use in pH measurement comprising:
an elongate body forming an internal chamber;
a silver wire in said chamber and coated with silver chloride;
a salt solution, surrounding said wire in said chamber;

means for making electrical contact with said current collector at one end of said body;

means forming a liquid junction structure at the other end of said body; and means at said liquid junction structure for promoting electrochemical contact between said salt solution and a test sample when said electrode is immersed in such a solution, said promoting means comprising a substantially ion impermeable mixture of anionic ion exchange polymer and cationic ion exchange polymer in which a substantial portion of the exchange sites in said polymers are occupied by equitransferant ions.

29. An electrode as claimed in claim 28, wherein said salt solution comprises a potassium chloride solution and said equitransferant ions on said polymers comprise potassium and chloride.

30. An electrode as claimed in claim 28, wherein said mixture comprises an anionic ion exchange polymer and a cationic ion exchange polymer.

31. An electrode as claimed in claim 30, wherein said anionic and cationic polymers are present in said mixture in substantially equivalent amounts.

32. An apparatus for measuring pH which comprises a reference electrode as claimed in any of claims 1, 5, 8 and 28, a measuring electrode and means for displaying said pH electrically connected to said reference and measuring electrodes, wherein said measuring electrode is sensitive to H+ ions and said reference electrode is insensitive to H+ ions.

33. A method of making a reference electrode which comprises:

incorporating a substantially ion-impermeable mixture of am anionic ion exchange polymer and a cationic ion exchange polymer in an electrode body comprising an elongate generally tubular member having a liquid-permeable structure across one end thereof, so that said polymer mixture is in contact with said structure; and incorporating in said electrode body an electrolyte, a half cell and means for making electrical connection to said half cell so that said electrolyte, half cell and polymer mixture are in electrochemical connection and said polymer mixture separates said liquid-permeable structure from said electrolyte and said half cell.

34. A method of making a reference electrode, as claimed in claim 33, which further comprises:

mixing anionic ion exchange polymer with cationic ion exchange polymer; and treating said polymers with an aqueous solution containing:
(a) ions of at least one member of the group consisting of halogen, nitrate and sulfate, and
(b) ions of at least one member of the group consisting of sodium, potassium, ammonium and calcium.

35. A method of making a reference electrode, as claimed in claim 33, wherein the anion of said anionic polymer comprises at least one member selected from the group consisting of halogen, nitrate and sulfate and the cation of said cationic polymer comprises at least one member selected from the group consisting of sodium, potassium, ammonium and calcium.

* * * * *